US010611891B2

(12) United States Patent
Hu et al.

(10) Patent No.: US 10,611,891 B2
(45) Date of Patent: Apr. 7, 2020

(54) TEXTILE WASTE PROCESSING

(71) Applicant: The Hong Kong Research Institute of Textiles and Apparel Limited, Kowloon (CN)

(72) Inventors: Yunzi Hu, Kowloon (CN); Carol Sze Ki Lin, Kowloon (CN); Shao-Yuan Leu, Kowloon (CN); Houde Jing, Kowloon (CN); Chi Shun Yeung, Kowloon (CN)

(73) Assignee: The Hong Kong Research Institute of Textiles and Apparel Limited, Kowloon (CN)

( * ) Notice: Subject to any disclaimer, the term of this patent is extended or adjusted under 35 U.S.C. 154(b) by 73 days.

(21) Appl. No.: 15/886,018

(22) Filed: Feb. 1, 2018

(65) Prior Publication Data

US 2019/0233610 A1 Aug. 1, 2019

(51) Int. Cl.
| | |
|---|---|
| *C08J 11/10* | (2006.01) |
| *C08J 11/08* | (2006.01) |
| *C12P 19/02* | (2006.01) |
| *C12P 19/14* | (2006.01) |
| *C08G 63/183* | (2006.01) |
| *D06M 16/00* | (2006.01) |

(52) U.S. Cl.
CPC ........... *C08J 11/105* (2013.01); *C08G 63/183* (2013.01); *C08J 11/08* (2013.01); *C12P 19/02* (2013.01); *C12P 19/14* (2013.01); *D06M 16/003* (2013.01); *C08J 2301/02* (2013.01); *C08J 2367/03* (2013.01); *C12Y 302/01004* (2013.01)

(58) Field of Classification Search
CPC ....... C08G 63/183; C08J 11/08; C08J 11/105; C08J 2301/02; C12P 10/02; C12P 19/04; C12Y 302/1004; D06M 16/003
See application file for complete search history.

(56) References Cited

U.S. PATENT DOCUMENTS

| | | | |
|---|---|---|---|
| 5,002,686 A | 3/1991 | Guth et al. | |
| 5,851,236 A | 12/1998 | Danner et al. | |
| 8,821,590 B2 | 9/2014 | Corbellini et al. | |
| 2006/0286268 A1 | 12/2006 | Shukla | |
| 2014/0343270 A1* | 11/2014 | Lindstrom | D01D 1/02 536/57 |

FOREIGN PATENT DOCUMENTS

| | | |
|---|---|---|
| CN | 102911395 A | 2/2013 |
| CN | 103556475 A | 2/2014 |
| CN | 104294609 A | 1/2015 |
| CN | 104499266 A | 4/2015 |
| CN | 104531234 A | 4/2015 |
| CN | 104532409 A | 4/2015 |
| CN | 105369637 A | 3/2016 |
| CN | 105780201 A | 7/2016 |

OTHER PUBLICATIONS

Gholamzad et al. Chem. Eng. J. (2014) 253: 40-45 (Year: 2014).*
Wang et al. Carb. Polymers (2008) 72: 178-184 (Year: 2008).*
Shen et al. Chem. Eng. Comm. (2008) 195: 1107-1121 (Year: 2008).*
Shen et al. (2008) Biochem. Engineer. J. 41: 241-250 (Year: 2008).*
International Patent Application No. PCT/CN2018/078576; Int'l Written Opinion and the Search Report; dated Nov. 1, 2018; 9 pages.
Jeoh et al.; "Cellulase digestibility of pretreated biomass is limited by cellulose accessibility"; Biotechnology and Bioengineering; 2007; vol. 98 No. 1; p. 112-122.
Kumar et al.; "Does change in accessibility with conversion depend on both the substrate and pretreatment technology?"; Bioresource Technology; 2009. 100(18); p. 4193-4202.
Sun et al.; "Hydrolysis of lignocellulosic materials for ethanol production: a review"; Bioresource technology; 2002; 83(1); p. 1-11.
Von Sivers et al.; "A techno-economical comparison of three processes for the production of ethanol from pine"; Bioresource technology; 1995; 51(1); p. 43-52.
Wyman et al.; "Coordinated development of leading biomass pretreatment technologies"; Bioresource technology; 2005; 96(18); p. 1959-1966.
Singh et al.; "Visualization of biomass solubilization and cellulose regeneration during ionic liquid pretreatment of switchgrass"; Biotechnology and Bioengineering; 2009; vol. 104 No. 1; p. 68-75.
Mäki-Arvela et al.; "Dissolution of lignocellulosic materials and its constituents using ionic liquids—a review"; Industrial Crops and Products; 2010; 32(3); p. 175-201.
Hong et al.; "Bacterial cellulose production from cotton-based waste textiles: enzymatic saccharification enhanced by ionic liquid pretreatment"; Bioresource Technology; 2012; 104; p. 503-508.
De Silva et al.; "Recycling textiles: the use of ionic liquids in the separation of cotton polyester blends"; RSC Advances; 2014; 4(55); 10 pages.
Zhao et al.; "Toxicity of ionic liquids"; Clean; 2007; 35(1): p. 42-48.
Fu et al.; "Aqueous ionic liquid pretreatment of straw"; Bioresource Technology; 2011; 102(13); p. 7008-7011.
Brodeur et al.; "Chemical and physicochemical pretreatment of lignocellulosic biomass: a review"; Enzyme research; 2011; vol. 2011; 18 pages.
Schacht et al.; "From plant materials to ethanol by means of supercritical fluid technology"; The Journal of Supercritical Fluids; 2008; 46(3); p. 299-321.
Gu et al.; "Supercritical CO2 and ionic liquids for the pretreatment of lignocellulosic biomass in bioethanol production"; Environmental technology; 2013; 34(13-14); p. 1735-1749.

(Continued)

*Primary Examiner* — Susan M Hanley
(74) *Attorney, Agent, or Firm* — Millen, White, Zelano & Branigan, PC; Ryan Pool

(57) ABSTRACT

Disclosed are methods for processing cotton containing textile waste that include alkaline pretreatment at freezing temperatures and a regeneration process. The method enhances cellulose digestion of the cotton to glucose and produces a solution containing glucose. In some aspects of the disclosed methods, the conversion yield of cotton to glucose can be as high as 80% or even 90%.

13 Claims, 8 Drawing Sheets

(56) References Cited

OTHER PUBLICATIONS

Saka et al.; "Chemical conversion of various celluloses to glucose and its derivatives in supercritical water"; Cellulose; 1999; 6(3); p. 177-191.
Muratov et al.; "Enzymatic hydrolysis of cotton fibers in supercritical $CO_2$"; Biotechnology and Bioprocess Engineering; 2002; vol. 7 No. 2; p. 85-88.
Hendriks et al.; "Pretreatments to enhance the digestibility of lignocellulosic biomass"; Bioresource Technology; 2009; 100(1); p. 10-18.
Carvalheiro et al.; "Hemicellulose biorefineries: a review on biomass pretreatments"; Journal of Scientific & Industrial Research; 2008; vol. 67; p. 849-864.
Fengel et al.; "Wood: chemistry, ultrastructure, reactions. Walter de Gruyter"; 1984; 613; 2 pages.
Charlotte et al.; "Carbohydrate composition analysis of bacterial polysaccharides: optimized acid hydrolysis conditions for HPAEC-PAD analysis"; Analytical Biochemistry; 1992; 201(2); p. 343-349.

\* cited by examiner

TEXTILE WASTE PROCESSING

FIELD

The present disclosure relates generally to textile waste treatment. More specifically, the present disclosure provides a textile waste treatment method with improved efficiency in the enzymatic hydrolysis of textile cotton into glucose.

BACKGROUND

Bioconversion of cellulose into glucose is an environmental approach to withdraw useful products from cotton based waste textile. Pretreatment of the feedstock is a primary and critical step to increase the cellulose accessibility to cellulase before enzymatic hydrolysis. Many pretreatment processes have been developed to reduce the recalcitrance of textile waste to enzymatic hydrolysis and furthermore decrease the consumption of cellulase. The basic approaches can be classified into four categories, i.e., chemical, biological, physical, and physico-chemical processes. Different pretreatment processes may result in different types and levels of structural modification and improve enzymatic hydrolysis after different mechanisms.

Acid pretreatment is currently the most widely studied and applied approach for the pretreatment of cellulose fibre and the other related feedstock. The key mechanisms of the acid pretreatment are the decomposition of the microstructure of cellulose fibres. The amorphous region of cellulose can be hydrolyzed while the crystalline regions with more reducing ends and non-reducing ends can be exposed to the enzymes, which facilitates the enzyme to perform degradation process. Acid pretreatment process, however, requires special reactors/container to prevent corrosion at elevated concentrations; and the acid reagents used are difficult to recycle. Both those factors can considerably increase the operation costs and environmental impacts of the overall biorefinery process. Meanwhile, high severity acid pretreatment (i.e., high acid doses, high temperature, and extended reaction time) can promote the conversion of carbohydrates to form into sugar dehydration by-products (i.e., furan-type inhibitors; 5-hydroxy methyl-furfural), which are harmful to the downstream fermentation processes at high concentration.

Another pretreatment method using ionic liquid (ILs) has drawn a significant amount of attention recently. There are mainly two factors lead to the various properties of ILs: the cation structure (the symmetrical array, the influence of alkylphosphonate and hydrophobic groups) and the anion delocalization degree. Some ILs have shown outstanding characteristics for industrial application, i.e. high chemical and thermal stabilities, liquid form in wide range of temperature, low vapour pressure, and low viscosity operation which reduces the cost of mixing. ILs have been tested in pretreating certain cotton or textile wastes, although its feasibility to large scale application is still unclear and needs further investigation. Hong, Guo used a 1-allyl-3-methyl-imidazolium chloride ([AMIM]Cl) IL to treat un-dyed 100% cotton t-shorts. After 90 minutes of pretreatment under 110° C. a high sugar yield (94%) was achieved by using reasonable amount of cellulase. De Silva et al. used the same IL to treat a 50:50 blend PET/cotton yard at a longer cooking period (6 hours) and higher temperature (120° C.). The cotton was effectively dissolved and regenerated in the anti-solvent and formed into fibre films after regeneration. The PET was completely recovered after the process. The key limiting factors hindering the applicability of ILs are high production cost and environmental toxicity. The current price for ([AMIM]Cl) IL is approximately US$22-26 per gram (chemical grade, Sigma-Aldrich). Furthermore, ILs have shown substantial negative influence on enzyme hydrolysis while the IL/cellulose mixture is difficult to handle in the existing reactor systems due to its high viscosity.

4-methylmorpholine 4-oxide (NMMO) is another solvent that can dissolve cellulose and provide reasonable yield. In NMMO process, heating at 80° C. under low water content leads to dissolution of higher molecular weight cotton fibres. However, NMMO concentrations above 5 and 25 g/L showed inhibition effects on enzymatic hydrolysis and fermentation. The treated materials must be washed before enzymatic hydrolysis and techno-economic studies showed that efficient recycling of NMMO is required in order to have an economically feasible process for pretreatment of cotton materials with NMMO. Certain side reactions present in the Lyocell process might affect the pretreatment system as well and lead to decomposition of NMMO, furthermore increasing the consumption of stabilizer. On the other hand, efficient removal of NMMO from the treated material by washing requires high amounts of water. This significant amount of water must be evaporated in an energy consuming process before reusing NMMO, which is an energy intensive process.

Supercritical fluid is a phase of reagents of which both gas and liquid phases coexist under a specific pressure and temperature. It shows liquid like density and gas like diffusing/penetrating ability to solid materials. Among all the supercritical fluids, supercritical carbon dioxide, which has a critical temperature at 31° C., has shown to be suitable for pretreatment of cellulosic feedstock. Supercritical carbon dioxide ($SC-CO_2$) has been widely used as an extraction solvent. In aqueous solution, $CO_2$ forms carbonic acid and can improve the hydrolysis of polymers. $CO_2$ molecule is similar in size as the molecules of water or ammonia, and therefore, they can penetrate through the same pathway to the small pores of the cellulose. $CO_2$ has even been used to modify steric structures of some cellulases to improve their stability, solvent tolerance and reactivity. Saka and Ueno investigated the direct conversion of various types of celluloses (including cotton linter) in supercritical water (500° C., 35 MPa) into glucose and found that cellulose can be hydrolyzed to a similar level as acid or enzymatic hydrolysis, without the difficulties associated with hydrolysing techniques. Muratov and Kim studied the performance of enzymatic hydrolysis of cotton fibres in supercritical $CO_2$ (120 atm, 50° C., 48 h) and found that the productivity of the glucose increased by 20% as compared to atmospheric conditions. As commercial scale of supercritical $CO_2$ treatment has been seen in textile industries (such as for dyeing), similar technology and equipment could be worthwhile to be explored further for the treatment of textile wastes in the future.

Alkaline pretreatment of textile waste can also be performed. During alkaline pretreatment, the first reactions that occur are solvation and saponification, of intermolecular ester bonds cross-linking which swells the textile to expose more accessible areas for the enzymes to hydrolyse the cellulose. However, a noticeable disadvantage of alkaline pretreatment is the formation of irrecoverable salts from alkaline or the combination of salts into the biomass which hinders the enzymatic hydrolysis. And alkaline pretreatment also works as another mechanism at ambient temperature at longer pretreatment time. At high alkaline concentration dissolution step, the effect of alkaline hydrolysis surpasses the alkaline dissolution, the 'peeling' of end-groups also hydrolyse the dissolved cellulose through degradation and decomposition cause the loss of polysaccharides. This increases the chance of loss of carbon, converting to carbon dioxide.

With all of the known pretreatment methods, the amount of enzyme loading required for the hydrolysis step is typically 20-30 FPU/g glucan. Accordingly, there remains a need for an improved textile waste treatment method that is more efficient, cheaper and which requires a lower enzyme loading.

SUMMARY

In one embodiment, the present disclosure provides a method of processing cotton containing textile waste comprising dissolution of textile waste in a NaOH/Urea solution at a predetermined temperature until freezing of the textile waste; adding an amount of an anti-solvent to regenerate cotton from the frozen textile waste; and hydrolysing said cotton with cellulase to produce a solution containing glucose.

The textile waste may be immersed in NaOH/Urea solution at or below 0° C., optionally for 6 hours. Preferably, the anti-solvent used in the regeneration step can be boiling water or ethanol.

Preferably, the cotton may be hydrolysed using an enzyme loading of ≤10 FPU/g glucan, and preferably an enzyme loading of 1-10 FPU/g glucan, and more preferably an enzyme loading of 5-10 FPU/g glucan.

In one embodiment, an enzymatic hydrolysis yield of cotton to glucose of over 80% is obtained following enzymatic hydrolysis.

Optionally, the method may further comprise the step of blending the textile waste, preferably by using a blender for 10-15 seconds.

In one embodiment, recovering PET fiber, and optionally recycling the recovered PET fiber may be preferred.

BRIEF DESCRIPTION OF THE FIGURES

The foregoing and other features and advantages of the disclosure will be apparent from the following, more particular description of embodiments of the disclosure, as illustrated in the accompanying drawings.

Figure 3A:
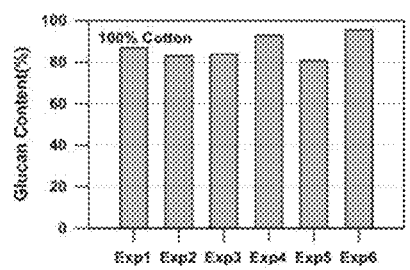
FIGS. 3A to 3E depict the released glucose concentration (g/L) of textile waste after being treated under different pretreatment experiment conditions (no. 1-6) as measured using NREL procedures. Since glucan is a polysaccharide of D-glucose monomers, the glucan content instead of the cellulose content was measured for evaluating the theoretical glucose amount yielded from the samples. The five cotton textile waste percentages are as follows: 100% cotton textile waste (FIG. 3A), 99% cotton textile waste percentage, 80% cotton textile waste (FIG. 3C), 60% cotton textile waste (FIG. 3D), and 40% cotton textile waste (FIG. 3E).
Figure 3B:
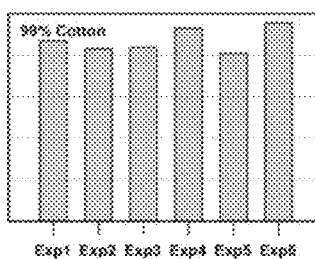
Figure 3C:
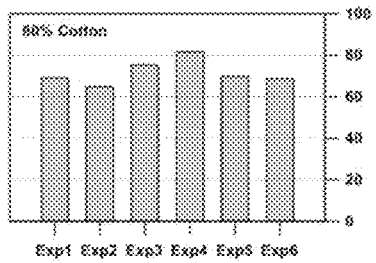
Figure 3D:
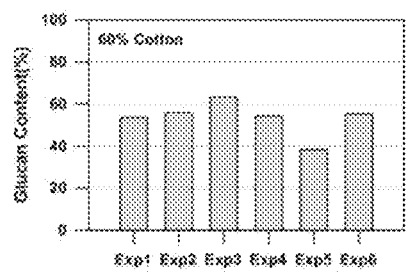
Figure 3E:
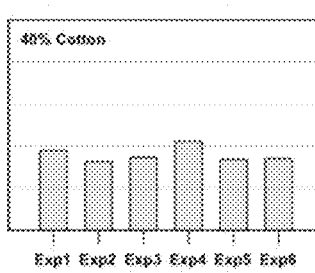

The five cotton textile waste percentages are as follows: 100% cotton textile waste (FIG. 3A), 99% cotton textile waste percentage, 80% cotton textile waste (FIG. 3C), 60% cotton textile waste (FIG. 3D), and 40% cotton textile waste (FIG. 3E).

Figure 5:
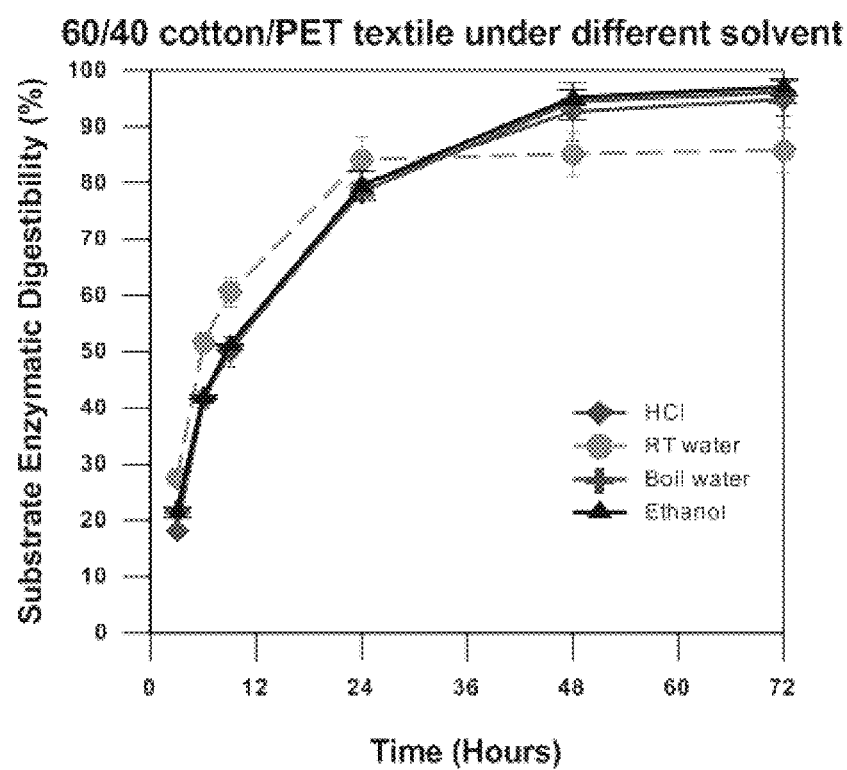

FIG. 5 depicts the substrate enzymatic digestibility (enzymatic hydrolysis yield) of 60/40 cotton/PET textile pretreated with NAOH/urea at freezing temperature followed by regeneration using different anti-solvents.

Figure 6:
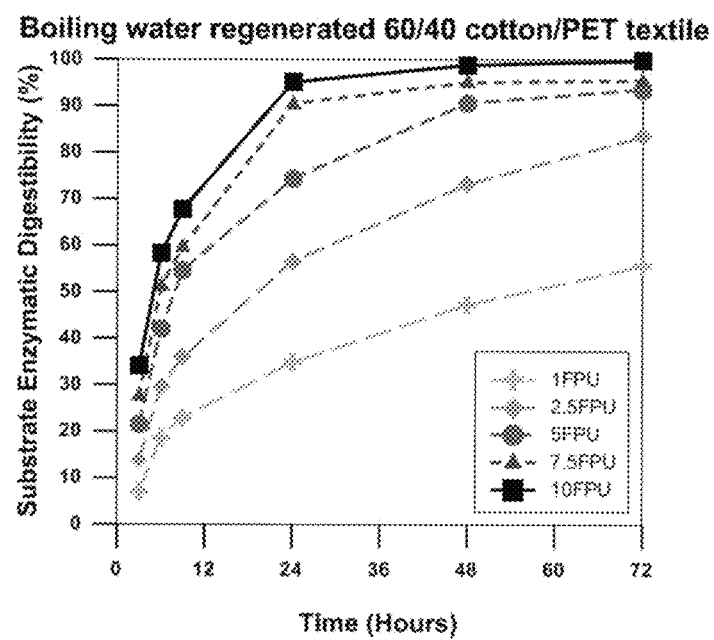

FIG. 6 depicts the substrate enzymatic digestibility (enzymatic hydrolysis yield) of pretreated 60/40 cotton/PET textile under different enzyme loading. The 60/40 cotton/PET textile was pretreated with NAOH/urea at freezing temperature followed by a regeneration step using boiling water.

Figure 7:
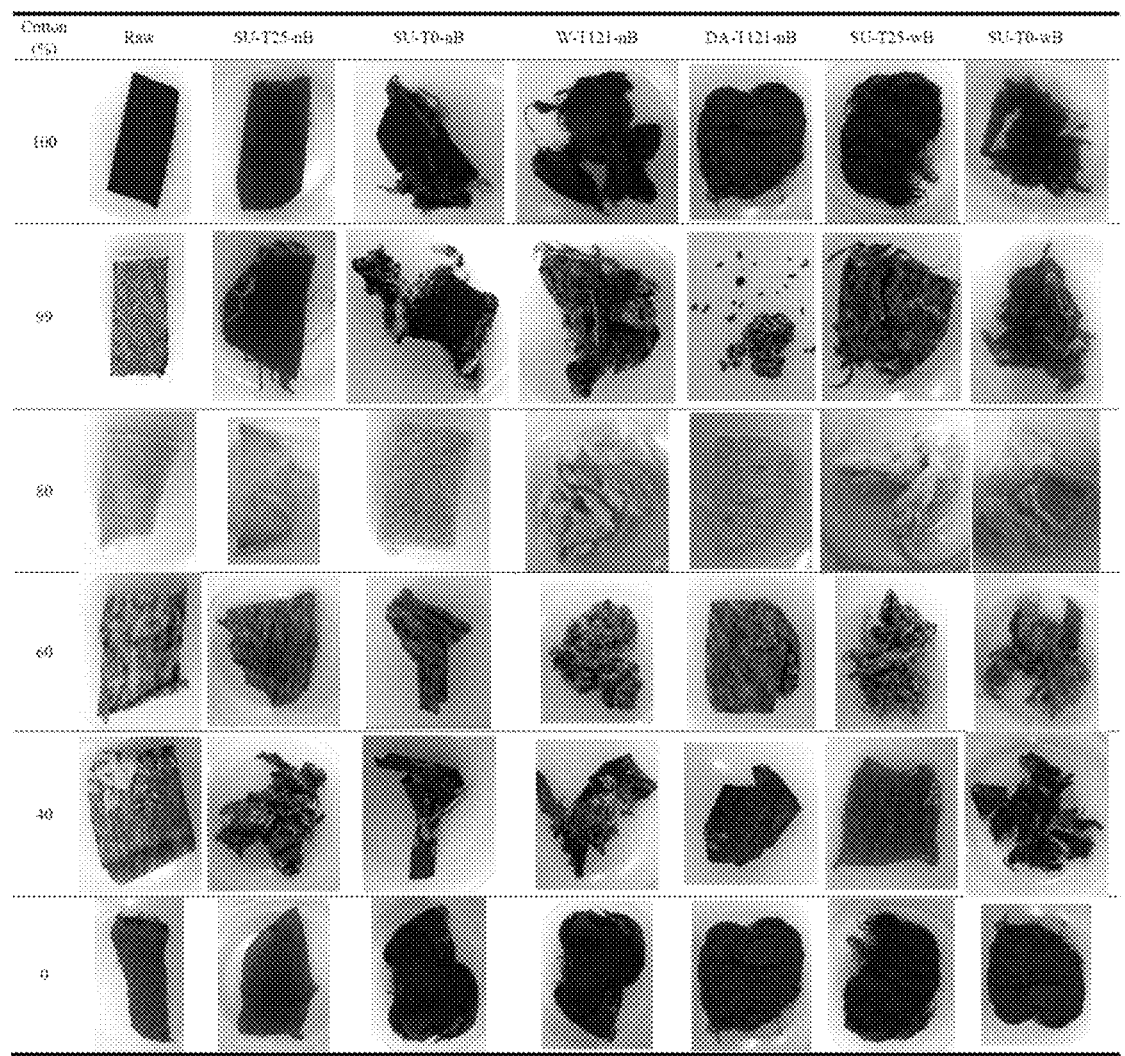

FIG. 7 is a set of photos showing the appearance changes of waste textile after pretreatment of water, dilute acid and NaOH/urea. "DA" denotes "dilute acid treatment (2% sulfuric acid)", "w" denotes "water", "SU" denotes "sodium hydroxide (7%) and urea (12%), "T" denotes temperature, "nB" denotes "not blended, and "wB" denotes "after blending).

Figure 8:
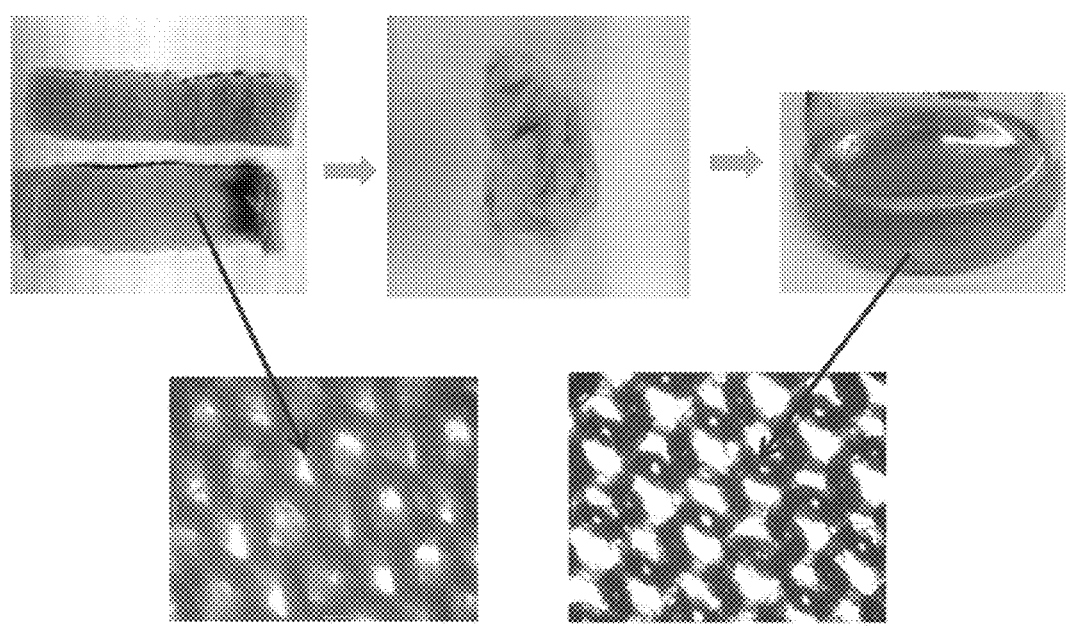

FIG. 8 is a set of photos showing the appearance of textile waste (Example 6: 80% cotton, 20% polyester under 0° C. with blending operation) before and after NaOH/urea pretreatment process. The microscopic images showed that after enzymatic digestion, the residue PET fiber was well preserved, indicating the possibility of recycling the PET for other uses.

DETAILED DESCRIPTION

The present disclosure provides a novel method of treating recycled textile waste (such as cotton/PET textile waste), which involves a modified alkaline pretreatment method. In an aspect of the present disclosure, the modified method comprises the steps of subjecting a textile waste to alkaline pretreatment with NaOH/urea at freezing temperatures, followed by a regeneration process.

Advantageously, the modified method is able to enhance cellulase digestion of cellulose to glucose. With this method, substrate enzymatic digestibility (SED) is significantly increased, allowing the use of a much lower enzyme loading as compared to conventional methods. At the same time, the conversion yield of cotton to glucose could be improved to over 80%, and over 90% for textile waste with high cotton percentage. It is also envisaged that the residue PET fiber can be extracted for other applications.

Figure 1:
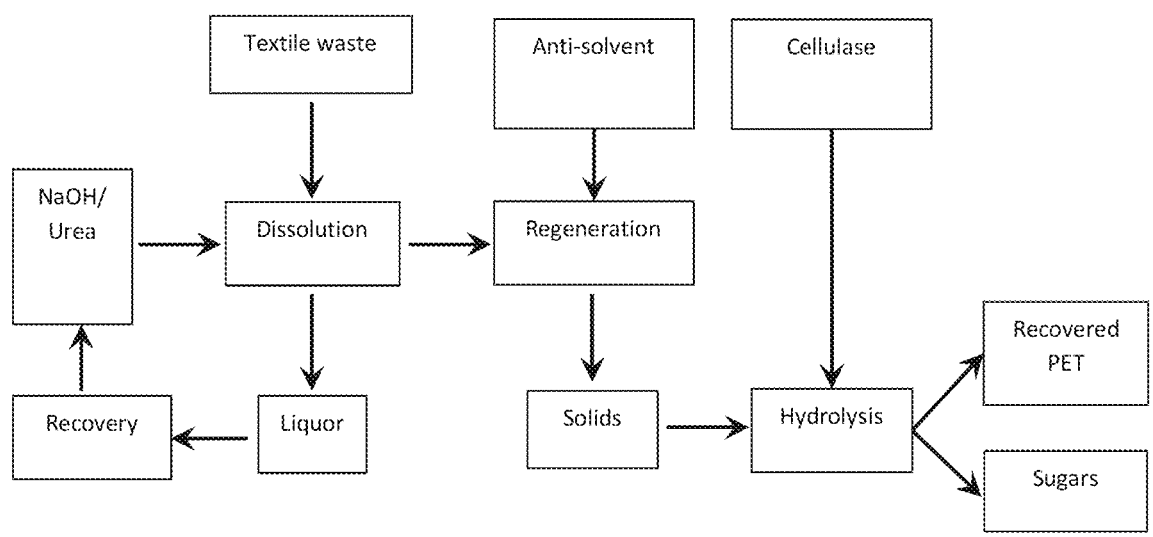
FIG. 1 is a block flow diagram of the textile waste process according to an embodiment of the disclosure. Dissolution and Regeneration in combination are being referred herein as the pretreatment step. The textile waste, following the pretreatment step, is subjected to hydrolysis by cellulose to recover PET and sugars.

Prior to enzymatic hydrolysis in recovery of glucose from the textile waste, the textile waste is first subjected to the novel pretreatment method which essentially comprises two steps as described below (and as shown in FIG. 1):

Step 1 (Dissolution Process):

Dissolution of textile waste in NaOH/Urea solution is preferred at freezing temperatures, for example, at or under 0° C., and more preferably between −5° C. to 0 until the textile waste is frozen. In an embodiment, the textile waste is immersed in 7% NaOH/12% Urea solution at 0° C.

This process typically takes 1-6 hours, and the alkaline is expected to cause a swelling effect to the cellulose, breaking down the inter and intra chains of cellulose molecules, resulting in more amorphous regions for enzymatic hydrolysis. This process reduces the DP and crystallinity index (CrI) of cellulose, increasing the cellulose accessibility to cellulase by creating more porous space for enzymatic hydrolysis.

Figure 2:
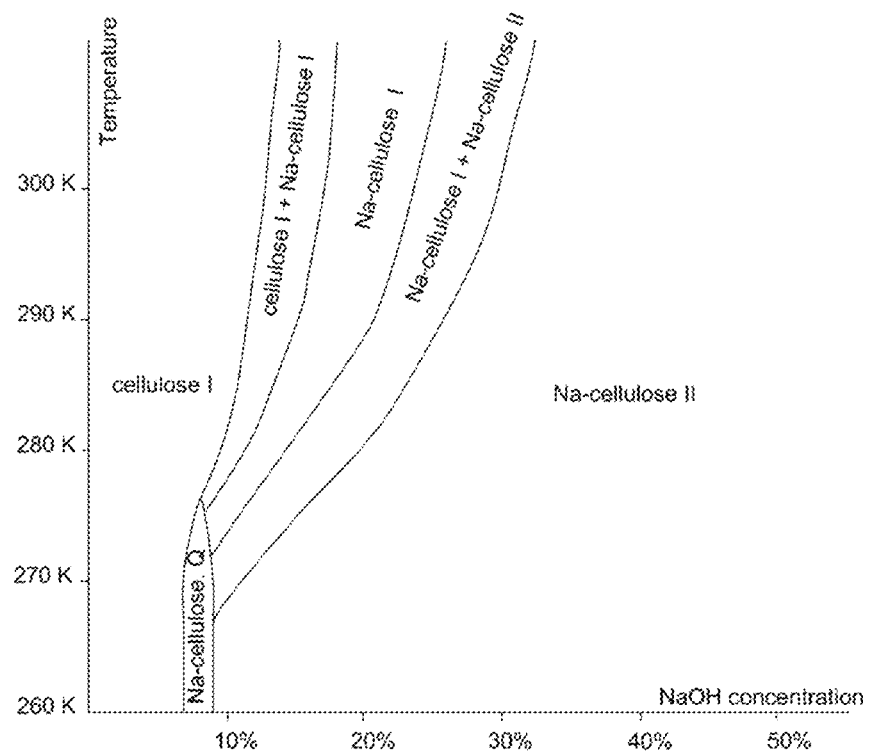
FIG. 2 is a Na-cellulose phase diagram from cotton soaking in NaOH solutions.

It is envisaged that an enhancement of substrate digestibility of the waste textile is achieved through cellulose dissolution process. This process was designed based upon the cellulose dissociation theory discovered previously, as shown in FIG. 2.

Step 2 (Regeneration Process):

Regeneration process has only been used in combination with textile waste pretreatment using ionic liquid (ILs) in the past. Regeneration using adding anti-solvents such as water, ethanol, or acetone in the regeneration process is necessary when the IL pretreatment has a dissolution effect on the cellulose.

When being applied in the present method, following the above alkaline pretreatment step, thawed (previously frozen) dissolved cellulose, is regenerated using anti-solvent(s), preferably boiling water or ethanol. The suitable amount of anti-solvent should be 2.5 times solvent mixture in volume.

It is expected that the regeneration of the cotton fiber is the key mechanism to increase the bioconversion efficiency of the textile waste. During the regeneration process morphological changes of cellulose can happen, with amorphous regions being increased. The dissolved cellulose can shrink to form a new allomorph structure (cellulose II). The crystallography of cellulose suggests that cellulose I comprises the parallel chains, whereas cellulose II is described as an antiparallel structure which is more enzyme accessible. The ability of NaOH to change the cellulose structure at lower temperature could be explained by a stronger binding between $Na^+$ and $OH^-$ to water at lower temperatures, enabling the breakage of the hydrogen bonds within the cellulosic structure.

It is expected that the regenerated cellulose with a lower degree of polymerization (DP from 2-6) has more β-glucosidic bonds accessible to cellulase. Regenerated cellulose is more water soluble than native cellulose prior to the regeneration. Therefore, it is expected that the regenerated cellulose can be hydrolyzed to short glucose oligomers in a shorter amount of time, contributing to an increased substrate enzyme digestibility (SED) and allowing a significantly lower enzyme loading to be used in the hydrolysis step Following the modified pretreatment process, the textile waste is then subjected to enzyme hydrolysis using cellulase. The hydrolysis step may be performed at any appropriate conditions, and preferable under 50° C., at pH 4.8 for 72 hours.

After cotton digestion, the remaining residue is mainly PET fiber, allowing simple extraction process to be performed in order to recycle the PET fiber in the textile waste.

Compared with conventional alkali pretreatment methods, the present method is able to achieve high conversion yield of cotton to glucose with a reduced enzyme loading, thereby significantly reducing overall costs. In one embodiment, an enzyme loading of as low as 5FPU/g glucan (and more preferably 5-10 FPU/g glucan) is sufficient to obtain a conversion yield that can normally be obtained using an enzyme loading is around 20-30 FPU/g glucan.

Additionally, compared with conventional methods using acid hydrolysis, NMMO and ionic liquid dissolution, the new method has notable benefits as follows:

1. Higher Enzymatic Digestibility

The present disclosure can solve the problem of achieving high enzymatic digestibility by decreasing the crystallinity of cotton. The significant increase in the disordered or amorphous fraction enhance the enzymatic digestibility as the cellulase protein can have greater accessibility to cellulose. In particular embodiments, the enzymatic digestibility can be over 80% for different cotton/PET composite fibres.

2. Lower Energy Consumption

The use of NMMO in textile waste pretreatment requires a pretreatment step at an elevated temperature of 80 to 120° C., as well as a step of NMMO solvent recycling, which involves high energy consumption. Both of these steps led to an increase in the total production cost.

On the other hand, the improved pretreatment process of the present disclosure includes a dissolution step performed at freezing temperatures (e.g. 0 to −5° C.), which can be easily accomplished in a standard, non-industrial freezer or in relatively cold countries. The use of such lower temperatures not only reduces energy consumption, but also avoids side reactions that may damage the PET, allowing the recycling of PET fiber from the textile waste with a simple extraction process. Additionally, the application of boiling water or ethanol as anti-solvent can lower the distillation energy.

3. Stability of Pretreatment Solution

The new pretreatment solution is stable in room temperature and low temperature (0° C.), therefore eliminating the need for chemical stabilizers, which are often required by other pretreatment methods. Therefore, the total cost of the chemicals required in the pretreatment process is also reduced.

The objects, advantages and features of the present disclosure will become more apparent when reference is made to the following examples taken in conjunction with the accompanying figures.

EXAMPLES

Aspects of the present disclosure demonstrated by the following examples that are demonstrative only and not intended to be limiting.

Materials

Waste textiles of five Cotton/PET ratios (i.e., 100% cotton, 99% cotton, 80% cotton, 60% cotton, and 40% cotton) as list in Table 1 were used as starting materials. These are being referred to as Samples 1-5 herein. All textile scrap samples were provided by H&M Far East. The samples were cut into rectangular pieces with 1 cm in dimension before further tests or analysis. Cellic CTEC II cellulase was generously provided by Novozymes China (Beijing). The initial activities towards filter paper and cellubioase were 70 FPU/mL and 450 CBU/mL. Commercial NaOH pellet (97%) and urea pellet (99%) were purchased from Sigma without any purification before use.

TABLE 1 collected textile waste composition

| Sample | Textile composition |
| --- | --- |
| 1 | 100% cotton |
| 2 | 99% cotton + 1% polyester |
| 3 | 80% cotton + 20% polyester |
| 4 | 60% cotton + 40% polyester |
| 5 | 40% cotton + 60% polyester |

Example 1

Pretreatment and Regeneration 2.5 g waste textile of each of the five textile waste samples is cut into smaller pieces in the size of 3 cm×3 cm squares and immersed into 100 g alkaline/urea solvents (NaOH/urea/water (7%/12%/81% wt), 100 g boiling water and 100 g 2% $H_2SO_4$ solution, respectively.

The samples obtained are kept under different temperatures, namely, 121° C., 25° C. and 0° C. as shown in Table 2 below. Each of the five textile samples (100% cotton, 99% cotton, 80% cotton, 60% cotton, 40% cotton) are subjected to six different experiment conditions, providing a total of 30 test samples.

For the samples pretreated at 0° C., the samples are placed in a freezer until it is fully frozen to dissolve the cellulose fibres (approximately 6 hours). As for controls, 100 g boiling water and 100 g 2% H$_2$SO$_4$ solution were adopted. It is well known that dilute acid method is the most widely used method for pretreating cellulosic material (for the purpose of releasing all the glucose for measurement). This is also the standard method described in NREL measurement procedure (2% H2SO4 for 1 hour at 121° C.). Blending was performed under experimental conditions 4 and 6, whereby a household blender was used to blend the substrates for 10-15 seconds.

TABLE 2

Pretreatment parameters use in the dissolution step

| Experiment Condition | Pretreatment Methods | Temperature/° C. | Process Time/ hour(s) |
|---|---|---|---|
| 1 | Water | 121 | 1 |
| 2 | 2% H$_2$SO$_4$/Unblend | 121 | 1 |
| 3 | 7% NaOH/12% Urea/Unblend | 25 | 12 |
| 4 | 7% NaOH/12% Urea/Blend | 25 | 12 |
| 5 | 7% NaOH/12% Urea/Unblend | 0 | 6 |
| 6 | 7% NaOH/12% Urea/Blend | 0 | 6 |

Following the alkaline/urea pretreatment process, the dissolved cellulose of all samples (with the exception of the controls) are regenerated by using boiling water as anti-solvent (amount of boiling water being 2.5 folds of solvent mixture in volume). The regenerated solids are then stirred using a 2-L lab-scale blender. Finally, the substrate is washed with deionised water until the sample pH is neutral, whereby the mixture is then filtrated to collect the solid, which is stored at 4° C. for further use. The overall pretreatment and regeneration process is shown in FIG. 1.

The pretreated substrate is freeze-dried and stored in a desiccator for following steps. The experiment design is shown in Table 2.

Example 2

Chemical Composition Analysis

Compositional analysis for all five samples is carried out by using the NREL procedure following by a HPAEC-PAD analysis. The untreated textile samples and pretreated substrates were ground into powder (by passing through a 60-mesh screen). In summary, acid insoluble content was calculated gravimetrically after digestion, and the concentrations of monosaccharides was determined by using a high-performance liquid chromatography (HPLC, Shimadzu) equipped with refractive index detector (RID). The monosaccharides (i.e., glucose,) were analyzed using an Aminex HPX-87P column (Bio-Rad) at 85° C. with 0.6 ml/min eluent of deionized water. The glucose concentration of the five samples following dissolution under different parameters are measured through HPLC and the results are shown in Table 3. The conversion of glucose can be calculated by using the equation 1 below.

TABLE 3

Released glucose concentration (g/L) of textile waste after different pretreatments by using NREL procedures.

| Experiment Condition | 100% Cotton | 99% Cotton + 1% PET | 80% Cotton + 20% PET | 60% Cotton + 40% PET | 40% Cotton + 60% PET |
|---|---|---|---|---|---|
| 1 | 3.109 | 3.029 | 2.466 | 1.883 | 1.338 |
| 2 | 2.902 | 2.155 | 2.264 | 1.999 | 1.142 |
| 3 | 2.948 | 2.538 | 2.645 | 2.247 | 1.226 |
| 4 | 3.283 | 2.631 | 2.853 | 1.941 | 1.511 |
| 5 | 2.789 | 2.282 | 2.475 | 1.321 | 1.180 |
| 6 | 3.143 | 2.30 | 2.429 | 1.973 | 1.209 |

$$\text{Glucose conversion} = \frac{G \times V}{\frac{W \times \text{glucan content}}{0.9}}. \quad \text{Equation 1}$$

Where G is glucose (mg/ml) concentration from HPLC analysis, V is the initial volume of biomass slurry (mL), W is the initial dry biomass weight. 0.9 is the conversion factor of glucose to equivalent glucan.

FIG. 3 showed the cellulose content in different types of textile waste by using NREL standard procedure.

Example 3

Enzymatic Hydrolysis

Enzymatic hydrolysis of lignocellulosic substrates was conducted at 2% (w/v) in 50 mL total volume which contains 2.5 mL 50 mM acetate buffer (pH 4.8), 0.4 ml Tetracycline in a shaking incubator at 50° C. and 200 rpm. The CTecII loading was 5 FPU/g glucan. Aliquots of 1.0 mL Samples were taken were taken periodically (3, 6, 9, 24, 48 and 72 h) for glucose analysis. Glucose concentration in hydrolysate was then determined by the glucose oxidase-peroxidase system using a commercial enzymatic assay kit.

Results

Substrate Digestibility on 100% Cotton Textile Waste (Sample 1)

100% cotton textile waste was pretreated as mentioned above using six different dissolution parameters and regenerated with boiling water as anti-solvent. The solid was further hydrolysed as mentioned in section 4.4. The glucose obtained during enzymatic hydrolysis was measured by a commercial enzymatic assay kit. The substrate digestibility at different time points (6, 24, 48 and 72 hours) were recorded. The substrate enzymatic digestibility means the percentage of glucan enzymatically hydrolyzed to glucose in 72 h at a 1% w/w substrate solid loading. The results are shown in Table 4.

TABLE 4

Substrate digestibility on 100% cotton textile waste pretreated under different experiment conditions as measured at different time points (6, 24, 48 and 72 hours)

| Experiment Condition | Pretreatment Methods | 6 hrs | 24 hrs | 48 hrs | 72 hrs |
|---|---|---|---|---|---|
| 1 | Water/121° C. | 4.2% | 5.0% | 5.9% | 5.9% |
| 2 | 2% H$_2$SO$_4$/Unblend | 8.7% | 10.9% | 12.0% | 12.8% |
| 3 | 7% NaOH/12% Urea/Unblend/25° C. | 6.6% | 10.1% | 12.8% | 14.2% |
| 4 | 7% NaOH/12% Urea/Blend/25° C. | 25.0% | 33.8% | 38.0% | 40.8% |
| 5 | 7% NaOH/12% Urea/Unblend/0° C. | 10.7% | 17.8% | 22.3% | 25.2% |
| 6 | 7% NaOH/12% Urea/Blend/0° C. | 62.7% | 81.2% | 83.9% | 86.7% |

Substrate Digestibility on 99%/1% Cotton/Elastane Textile Waste (Sample 2)

Textile waste of 99%/1% cotton/elastane was pretreated as mentioned above using six different dissolution parameters and regenerated with boiling water as anti-solvent. The solid was further hydrolysed as mentioned above. The glucose obtained during enzymatic hydrolysis was measured by a commercial enzymatic assay kit. The substrate digestibility at different time points (6, 24, 48 and 72 hours) were recorded. The results are shown in Table 5.

TABLE 5

Substrate digestibility on 99%/1% cotton/PET waste textiles under different experiment conditions as measured at different time (6, 24, 48 and 72 hours)

| Experiment Condition | Pretreatment Methods | 6 hrs | 24 hrs | 48 hrs | 72 hrs |
|---|---|---|---|---|---|
| 1 | Water/121° C. | 10.4% | 12.3% | 13.8% | 14.3% |
| 2 | 2% H$_2$SO$_4$/Unblend | 17.9% | 26.4% | 33.0% | 36.8% |
| 3 | 7% NaOH/12% Urea/Unblend/25° C. | 18.7% | 34.8% | 47.4% | 55.1% |
| 4 | 7% NaOH/12% Urea/Blend/25° C. | 50.5% | 73.1% | 83.9% | 91.7% |
| 5 | 7% NaOH/12% Urea/Unblend/0° C. | 19.7% | 24.5% | 36.5% | 44.4% |
| 6 | 7% NaOH/12% Urea/Blend/0° C. | 64.7% | 86.1% | 90.8% | 95.9% |

Substrate Digestibility on 80%/20% Cotton/PET Textile Waste (Sample 3)

Cotton/PET 80/20 textile waste was pretreated as mentioned above using six different dissolution parameters and regenerated with boiling water as anti-solvent. The solid was further hydrolysed as mentioned in Section 4.4. The glucose obtained during enzymatic hydrolysis was measured by a commercial enzymatic assay kit. The substrate digestibilities at different time points (6, 24, 48 and 72 hours) were recorded. The results are shown in Table 6.

TABLE 6

Substrate digestibility on 80/20 cotton/PET textile wastes under different experiment conditions as measured at different time points (6, 24, 48 and 72 hours).

| Experiment Condition | Pretreatment Methods | 6 hrs | 24 hrs | 48 hrs | 72 hrs |
|---|---|---|---|---|---|
| 1 | Water/121° C. | 11.6% | 14.4% | 16.2% | 19.5% |
| 2 | 2% H$_2$SO$_4$/Unblend | 11.5% | 28.5% | 39.8% | 50.0% |
| 3 | 7% NaOH/12% Urea/Unblend/25° C. | 18.7% | 34.0% | 46.3% | 54.1% |
| 4 | 7% NaOH/12% Urea/Blend/25° C. | 66.6% | 83.6% | 88.3% | 89.5% |
| 5 | 7% NaOH/12% Urea/Unblend/0° C. | 26.5% | 49.3% | 63.5% | 69.7% |
| 6 | 7% NaOH/12% Urea/Blend/0° C. | 72.8% | 91.1% | 93.9% | 94.1% |

Substrate Digestibility on 60/40 Cotton/PET Textile Waste (Sample 4)

Cotton/PET 60/40 textile waste was pretreated as mentioned above using six different dissolution parameters and regenerated with boiling water as anti-solvent. The solid was further hydrolysed as mentioned in Section 4.4. The glucose obtained during enzymatic hydrolysis was measured by a commercial enzymatic assay kit. The substrate digestibilities at different time points (6, 24, 48 and 72 hours) were recorded. The results are shown in Table 7.

TABLE 7

Substrate digestibility on 60/40 cotton/PET textile waste under different experiment conditions as measured at different time points (6, 24, 48 and 72 hours)

| Experiment No. | Pretreatment Methods | 6 hrs | 24 hrs | 48 hrs | 72 hrs |
|---|---|---|---|---|---|
| 1 | Water/121° C. | 5.3% | 8.3% | 10.0% | 11.5% |
| 2 | 2% $H_2SO_4$/Unblend | 13.3% | 15.9% | 20.4% | 23.5% |
| 3 | 7% NaOH/12% Urea/Unblend/25° C. | 17.0% | 32.9% | 40.8% | 46.4% |
| 4 | 7% NaOH/12% Urea/Blend/25° C. | 24.8% | 43.7% | 58.2% | 65.3% |
| 5 | 7% NaOH/12% Urea/Unblend/0° C. | 48.8% | 80.0% | 85.9% | 87.4% |
| 6 | 7% NaOH/12% Urea/Blend/0° C. | 46.4% | 74.2% | 79.1% | 80.9% |

Substrate Digestibility on 40/60 Cotton/PET Textile Waste (Sample 5)

Cotton/PET 40/60 textile waste was pretreated as mentioned above using six different dissolution parameters and regenerated with boiling water as anti-solvent. The solid was further hydrolysed as mentioned in Section 4.4. The glucose obtained during enzymatic hydrolysis was measured by a commercial enzymatic assay kit. The substrate digestibility at different time points (6, 24, 48 and 72 hours) were recorded. The results are shown in Table 8.

TABLE 8

Substrate digestibility on 40/60 cotton/PET textile waste under different experiment conditions as measured at different time points (6, 24, 48 and 72 hours)

| Experiment Condition | Pretreatment Methods | 6 hrs | 24 hrs | 48 hrs | 72 hrs |
|---|---|---|---|---|---|
| 1 | Water/121° C. | 5.4% | 7.9% | 8.5% | 8.5% |
| 2 | 2% $H_2SO_4$/Unblend | 11.9% | 21.1% | 26.7% | 31.9% |
| 3 | 7% NaOH/12% Urea/Unblend/25° C. | 12.2% | 26.4% | 34.7% | 40.3% |
| 4 | 7% NaOH/12% Urea/Blend/25° C. | 20.8% | 37.4% | 49.5% | 59.0% |
| 5 | 7% NaOH/12% Urea/Unblend/0° C. | 55.5% | 86.3% | 88.3% | 88.0% |
| 6 | 7% NaOH/12% Urea/Blend/0° C. | 50.7% | 84.9% | 86.9% | 88.6% |

From the results of Table 2-6, pretreatment method using freezing soda/urea in combination with a regeneration step, followed by blending showed the highest substrate digestibility. Over 80% of cotton cellulose has been digested within 24-72 hours for all 5 different Cotton/PET samples. Noticeably, in regards to the 99%/1% cotton/PET waste textiles (sample 2) and the 80%/20% cotton/PET textile waste (sample 3), it was found that 95.9% and 94.1% of cotton cellulose were digested within 72 hours, respectively.

Figures 4A, 4B, 4C:
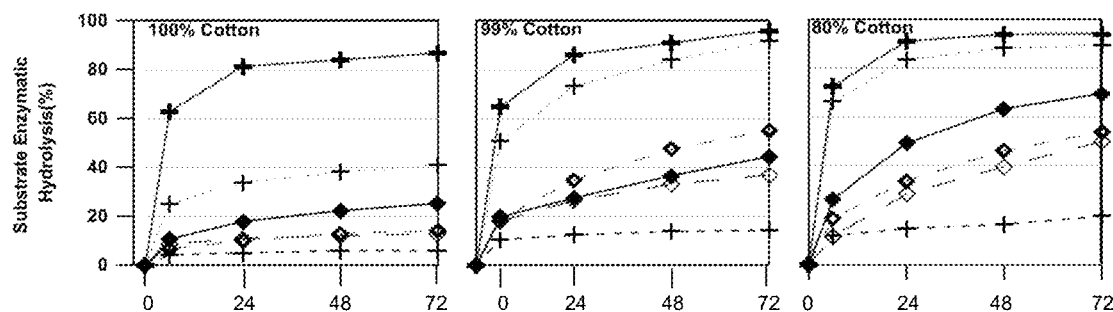
FIGS. 4A-4E show the substrate enzymatic hydrolysis (enzymatic hydrolysis yield) of different textiles samples pretreated under different experiment conditions (no. 1-6) as measured at different time points (6, 24, 48 and 72 hours).
Figures 4D, 4E:
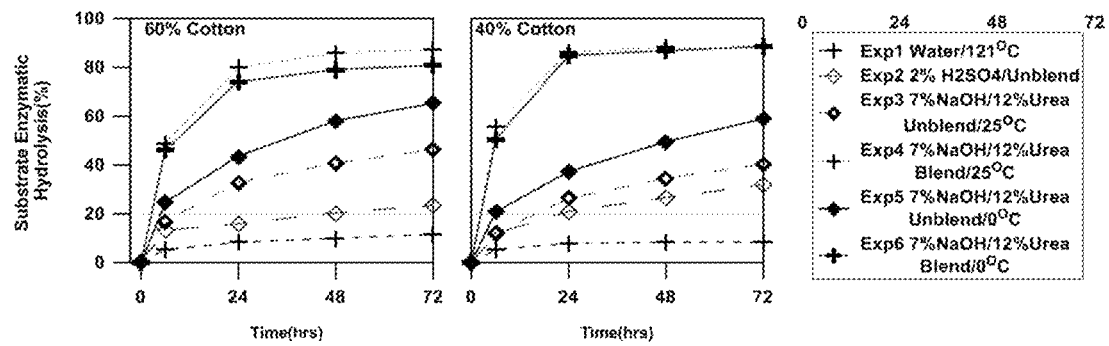

As shown in FIG. 4, even without the blending step, substrate digestibilities were found to be consistently higher when the pretreatment method combining a dissolution step using freezing soda/urea and a regeneration step was adopted (Samples 3-5).

Other pretreatment methods using water with high temperature or dilute acid showed low degree of enzymatic digestion.

Therefore, the textile wastes treated with this novel pretreatment process demonstrate better effect on increasing the cotton digestibility and further allow the PET residue to be more easily collected after the digestion of cotton. As noted in Table 2, as compared to NaOH/urea pretreatment at 25° C., the new pretreatment process can be performed at a more efficient manner, since the textile wastes are only immersed in NaOH/urea for 6 hours.

FIG. 4 shows comparison on substrate enzymatic hydrolysis of different textile with different pretreatments within 72 hours.

Example 4

Effect of Regeneration Process

The following experiment was conducted to demonstrate the effect of the regeneration process on the efficiency of cellulose recovery. After dissolving the textile waste in NaOH/urea as described in Example 1 above using experiment condition 6 (7% NaOH/12% Urea/Blend), frozen cellulose/dissolved textile solvent was first thawed, subsequently, boiling water, room temperature (RT) water or ethanol was slowly poured into the thawed solvent respectively and stirred for 3 minutes. The samples were then washed to pH=7 by using deionized water. The control experiment of regeneration were conducted by directly adjusting the thawed solvent to neutral by 10 M HCl solution for further use.

Table 9 below shows the glucan content of the samples after different solvent methods. It was observed that the HCL neutralization method resulted in the highest loss of glucan content (around 17%) due to the missing step of regeneration. By contrast, the boiling water regeneration process recovered the highest content of the glucan.

TABLE 9

Glucan content after regeneration using different solvent methods as measured by chemical composition analysis.

| Sample | Solvent types being used for regeneration | Glucan content (%) |
|---|---|---|
| 1 | 10M HCl neutralization | 32.97% |
| 2 | Room temperature water | 46.33% |
| 3 | Boiling water | 50.14% |
| 4 | Ethanol | 49.39% |
| 5 | control | 51.67% |

To demonstrate the significance of the regeneration process, enzymatic hydrolysis analysis of the 60/40 textile waste sample pretreated under experimental condition 6 (7% NaOH/12% Urea/Blend) was conducted to compare the substrate enzymatic digestibility (hydrolysis yield) of different samples when being regenerated using different anti-solvents. The results are shown in FIG. 5.

It can be observed that freezing soda process largely increased the substrate enzymatic digestibility regardless of the anti-solvent selected for regeneration. However, regeneration using boiling water and ethanol are found to be the most effect way to further increase the enzymatic hydrolysis yield.

Although HCl neutralization resulted in high enzymatic hydrolysis yield, it should be noted that the glucan content that can be recovered using this method is much lower (see Table 9).

As further illustrated in FIG. 6, when pretreatment is carried out using NaOH/urea at freezing temperature and when boiling water is selected as the anti-solvent for regeneration, an enzyme loading at 5 FPU/g glucan is sufficient to achieve over 90% substrate enzyme digestibility. This further highlights the unexpected superior SED of textile waste achieved by using the pretreatment process as disclosed herein.

Example 5

Microscope Image of Textile Before and after the Pretreatment.

FIG. 7 is a set of photos recording the textile appearance throughout the pretreatment process.

A 80% cotton/20% PET sample has been observed under microscope to investigate the difference in appearance before and after NaOH/urea pretreatment (7% NaOH/12% Urea, under 0° C. with blending operation). As demonstrated in FIG. 8, the photos showed that after enzymatic digestion, the residue PET fiber was still preserved, indicating the potential of such being recycled for other applications.

The experimental data presented herein demonstrates that, by subjecting textile waste to a modified pretreatment process combining a dissolution step with NaOH/urea at freezing temperature and a regeneration step, it is possible to achieve high conversion yield of cotton to glucose with a reduced enzyme loading. It has been shown that an enzyme loading of SFPU/g-10 FPU/g glucan (and as low as SFPU/g glucan) is sufficient to achieve a conversion yield of 90%, therefore significantly reducing the amount of enzyme loading required. A person skilled in the art would appreciate that the presently claimed pretreatment method allows the substrate enzyme digestibility of textile waste to be achieved in a more efficient and effective manner, and at a reduced overall cost.

The invention claimed is:

1. A method of processing cotton containing textile waste comprising:
    dissolution of textile waste in a NaOH/Urea solution at a predetermined temperature until freezing of the textile waste;
    adding an amount of an anti-solvent selected from boiling water and ethanol to regenerate cotton from the frozen textile waste; and
    hydrolysing said cotton with cellulase to produce a solution containing glucose.

2. The method according to claim 1, wherein the textile waste is immersed in NaOH/Urea solution at or below 0° C.

3. The method according to claim 2, wherein the textile waste is immersed in NaOH/Urea solution for 6 hours.

4. The method according to claim 1, wherein hydrolysing is performed using an enzyme loading of ≤10 FPU/g glucan.

5. The method according to claim 1, wherein hydrolysis is performed using an enzyme loading of 1-10 FPU/g glucan.

6. The method according to claim 1, wherein hydrolysis is performed using an enzyme loading of 5-10 FPU/g glucan.

7. The method according to claim 1, wherein an enzymatic hydrolysis yield of cotton to glucose of over 80% is obtained following enzymatic hydrolysis.

8. The method according to claim 1, wherein the method further comprises blending the textile waste.

9. The method according to claim 8, wherein blending of the textile waste is performed using a blender for 10-15 seconds.

10. The method according to claim 1, wherein the method further comprises recovering polyethylene terephthalate (PET) fiber.

11. The method according to claim 10, wherein the method further comprises recycling the PET fiber.

12. The method according to claim 1, wherein the anti-solvent is boiling water.

13. The method according to claim 1, wherein the anti-solvent is ethanol.

* * * * *